United States Patent
Ayliffe et al.

(10) Patent No.: US 9,470,616 B2
(45) Date of Patent: Oct. 18, 2016

(54) PIPETTE INSTRUMENT

(75) Inventors: Harold E. Ayliffe, Hailey, ID (US); Michael E. McGinnis, Duvall, WA (US); Curts S. King, Kirkland, WA (US)

(73) Assignee: E.I. SPECTRA, LLC, Ketchum, ID (US)

( * ) Notice: Subject to any disclaimer, the term of this patent is extended or adjusted under 35 U.S.C. 154(b) by 1027 days.

(21) Appl. No.: 13/266,450

(22) PCT Filed: Apr. 27, 2009

(86) PCT No.: PCT/US2009/002564
§ 371 (c)(1),
(2), (4) Date: Oct. 26, 2011

(87) PCT Pub. No.: WO2010/126459
PCT Pub. Date: Nov. 4, 2010

(65) Prior Publication Data
US 2012/0046883 A1    Feb. 23, 2012

(51) Int. Cl.
*B01L 3/02* (2006.01)
*G01N 15/12* (2006.01)
*G01N 35/10* (2006.01)

(52) U.S. Cl.
CPC ............ *G01N 15/12* (2013.01); *B01L 3/021* (2013.01); *B01L 3/0237* (2013.01); *B01L 2200/141* (2013.01); *B01L 2200/143* (2013.01); *B01L 2200/146* (2013.01); *B01L 2400/0487* (2013.01); *G01N 2035/1062* (2013.01)

(58) Field of Classification Search
CPC ..................................... B01L 3/021
USPC .......................................... 702/26
See application file for complete search history.

(56) References Cited

U.S. PATENT DOCUMENTS

| | | | |
|---|---|---|---|
| 3,910,702 A * | 10/1975 | Corll | ............. 356/72 |
| 4,734,261 A | 3/1988 | Koizumi et al. | |
| 5,133,218 A | 7/1992 | Uffenhiemer et al. | |
| 5,432,098 A | 7/1995 | Wilks | |
| 5,443,791 A | 8/1995 | Cathcart et al. | |
| 5,504,011 A | 4/1996 | Gavin et al. | |
| 5,509,318 A | 4/1996 | Gomes | |
| 5,837,199 A | 11/1998 | Dumschat | |
| 6,244,119 B1 | 6/2001 | Theran | |
| 6,702,990 B1 | 3/2004 | Camacho et al. | |
| 6,816,257 B2 | 11/2004 | Goix | |
| 6,838,278 B2 | 1/2005 | Fortino | |

(Continued)

FOREIGN PATENT DOCUMENTS

| JP | 10318904 | 12/1998 |
|---|---|---|
| JP | 2000275163 | 10/2000 |

*Primary Examiner* — Bryan Bui
(74) *Attorney, Agent, or Firm* — Foster Pepper PLLC; P. G. Scott Born

(57) ABSTRACT

A pipette instrument 100 carrying interrogation circuitry 132 adapted to interrogate a data signal received from a removable instrumented pipette tip 114. The pipette 100 includes a microprocessor and memory 130 that can be programmed to perform data collection procedures. User controls typically include a start button 108, and a track wheel 110. A display device 112 can present device options through one or more menu, and show data resulting from one or more test result. The pipette can interrogate particles carried by a fluid flowing through a tip 114 by detecting either of or both of Coulter principle phenomena, and Stokes-shift phenomena.

20 Claims, 9 Drawing Sheets

(56) References Cited

U.S. PATENT DOCUMENTS

| | | | |
|---|---|---|---|
| 6,874,379 B2 | 4/2005 | Matsuda et al. | |
| 7,005,109 B2 | 2/2006 | Husar | |
| 7,093,507 B2 | 8/2006 | Thom et al. | |
| 7,520,164 B1 * | 4/2009 | Ayliffe | G01N 15/1056 324/71.1 |
| 7,794,664 B2 | 9/2010 | Pelletier et al. | |
| 7,835,000 B2 | 11/2010 | Graves et al. | |
| 7,955,865 B2 | 6/2011 | Marziali et al. | |
| 8,015,887 B2 | 9/2011 | Ayliffe et al. | |
| 8,153,949 B2 | 4/2012 | Kiesel et al. | |
| 2002/0176803 A1 | 11/2002 | Hamel et al. | |
| 2005/0232819 A1 | 10/2005 | Jagdhuber | |
| 2007/0143033 A1 * | 6/2007 | Zhang et al. | 702/26 |
| 2008/0253934 A1 | 10/2008 | DiTrolio et al. | |
| 2009/0000350 A1 | 1/2009 | Magnussen et al. | |
| 2009/0000403 A1 * | 1/2009 | Magnussen et al. | 73/864.18 |
| 2009/0014360 A1 | 1/2009 | Toner et al. | |
| 2009/0070049 A1 | 3/2009 | Ziegler et al. | |
| 2009/0071266 A1 | 3/2009 | Nelson et al. | |
| 2009/0074790 A1 | 3/2009 | Reiss et al. | |
| 2009/0272179 A1 | 11/2009 | Ayliffe | |
| 2010/0028207 A1 * | 2/2010 | Colella et al. | 422/73 |
| 2010/0132486 A1 | 6/2010 | Millet et al. | |
| 2010/0199788 A1 | 8/2010 | Ayliffe et al. | |
| 2010/0216126 A1 | 8/2010 | Balachandran et al. | |
| 2010/0230284 A1 | 9/2010 | Stephenson | |
| 2010/0291584 A1 | 11/2010 | Tseng et al. | |
| 2011/0182781 A1 | 7/2011 | Dzuong | |
| 2011/0182782 A1 | 7/2011 | Dzuong | |

* cited by examiner

PIPETTE INSTRUMENT

TECHNICAL FIELD

This invention relates to devices that may be used repetitively to extract a precise volume of fluid from a bulk container of fluid.

BACKGROUND

A pipette is arguably one of the most commonly used hand tools in a wet chemistry laboratory environment. Typically, a pipette is used to extract one or more sub-sample from a bulk container of fluid. (This disclosure will generally make specific reference to a pipette tip, in an attempt to distinguish the removable tip over the pipette instrument itself). Pipettes are commercially available in various configurations that may be used repetitively to extract and dispense precisely metered quantities of fluid. Commercially available pipettes include both hand-held models and benchtop models that may be variously automated, or robotically controlled.

Recent United States patents disclosing various pipette devices include: U.S. Pat. No. 7,448,287 to Daniel et al.; U.S. Pat. No. 7,438,861 to Hochstrasser et al.; U.S. Pat. No. 7,434,484 to Belgardt; U.S. Pat. No. 7,416,704 to Scordato et al.; U.S. Pat. No. 7,182,915 to Bullen et al.; U.S. Pat. No. 6,997,062 to Cronenberg; and U.S. Pat. No. 6,582,664 to Bevirt et al. All of the above-referenced documents are hereby incorporated by reference, as though set forth herein in their entireties, for their disclosures of relevant technology and various pipette arrangements.

Certain sensing devices that may be employed in selected aspects of the instant invention are disclosed in the co-owned International patent applications serial No. PCT/US 09/02172, filed 7 Apr. 2009, titled "METHOD FOR MANUFACTURING A MICROFLUIDIC SENSOR", and serial No. PCT/US 08/11205, filed 26 Sep. 2008, titled "INSTRUMENTED PIPETTE TIP". Details of construction of certain relevant devices structured to detect Stokes-shift phenomena are disclosed in co-owned International Patent application serial No. PCT/US 08/13003, titled "FLUORESCENCE-BASED PIPETTE INSTRUMENT", and filed on 21 Nov. 2008, which claims priority to U.S. Provisional Patent Application Ser. No. 61/004,630, filed Nov. 27, 2007, for "Fluorescence-based pipette instrument". All of the above-referenced documents are hereby incorporated by reference, as though set forth herein in their entireties, for their disclosures of relevant technology.

DISCLOSURE OF THE INVENTION

The present invention provides an apparatus and method for interrogating particles that are suspended in a fluid. A currently preferred apparatus is embodied as a pipette instrument, and may interrogate particles in a fluid sample as the sample is extracted from a bulk container of particle-bearing fluid.

An exemplary pipette instrument includes a body carrying a source of suction, a pipette tip interface, and a source of electrical energy such as a battery. An operable pipette tip interface is configured to hold a removable pipette tip and to place an installed pipette tip into communication with the source of suction. Desirably, the pipette tip interface is arranged to dispose an installed pipette tip in communication with interrogation circuitry configured to receive an input signal from an installed pipette tip. The pipette instrument also includes a display panel capable of visually presenting information to a user, and a microprocessor and an associated memory.

Sometimes, a pipette instrument includes a hydrophobic barrier element disposed to resist flow of fluid from an installed pipette tip past the barrier element and further into the pipette instrument. Typically, a pressure transducer is disposed in communication with the microprocessor to monitor a suction pressure profile delivered to the pipette tip interface. Certain pipette instruments include a USB port structured to permit communication between the pipette instrument and a remote terminal. It is within contemplation to provide a wireless communication module structured to permit communication between the pipette instrument and a remote terminal. Software may be loaded into the memory effective to program the microprocessor to permit the pipette instrument to perform a selected test.

Preferred pipette instruments include a user control system operable to select a desired mode of operation of the pipette instrument from a plurality of operable modes. One user operable control system includes a track wheel, and a start button. A track wheel can be disposed to interface for actuation by rolling along a length axis of a finger of a hand that is holding the pipette body such that the wheel is disposed in registration with a distal portion of a user's finger. Also, the track wheel may be structured to provide an input to the pipette instrument by permitting a finger to depress the track wheel in a trigger-squeezing motion.

One operable source of suction includes a surplus vacuum in a reservoir, and a regulator operable to down-regulate that surplus vacuum disposed for action between the reservoir and pipette tip interface effective to place a desired vacuum profile in communication with an installed pipette tip. Surplus vacuum may be created by user displacement of a biased element associated with the body. Surplus vacuum can also be created with an electric pump. A preferred source of suction comprises an electric pump operable under control of the microprocessor directly to generate an actual desired suction profile delivered to the pipette tip interface.

Desirably, the pipette instrument's body carries interrogation circuitry. Preferred interrogation circuitry is adapted for detecting particles moving through a pipette tip that is installed in the pipette tip interface. Certain interrogation circuitry is adapted for particle counting by detection of signals resulting from Stokes-shift phenomena occurring in the pipette tip. Certain interrogation circuitry is adapted for particle counting by detection of signals resulting from Coulter principle phenomena occurring in the pipette tip. Desirably, a hand-held portion of the pipette instrument is configured both to apply a first signal to an installed pipette tip and to receive a second signal from the pipette tip, with the second signal being different from the first signal.

Certain aspects of the instant invention provide a method for particle counting. One such method includes providing a pipette instrument; installing a pipette tip effective to place a sensor component of the pipette tip in communication with interrogation circuitry carried by the pipette instrument; and using the pipette instrument to apply a first signal to the sensor component. The method may also include generating a raw histogram based at least in part upon a second signal received from the sensor component of the pipette tip as a sample of particle-bearing fluid flows through the pipette tip. The method may further include performing a determination based on at least a portion of the raw histogram to obtain one or more observed particle count, and outputting that one or more observed particle count to a display terminal. The method may also include selecting a lower threshold boundary, selecting an upper threshold boundary, and calculating a particle count based upon data collected between the selected boundaries. Sometimes, the method includes performing a mathematical computation on the observed particle count to determine a true particle count. The method may include obtaining a corrected histogram based on a mathematical analysis of the raw histogram and a probability that at any instant there is more than one particle in an interrogation zone of the sensor component. The method may include applying a correction factor, incorporating one or more calibration histogram associated with the sensor component, to the raw histogram to obtain a particle count. Certain times, the method may include collecting sufficient data to determine a volumetric particle count.

These features, advantages, and alternative aspects of the present invention will be apparent to those skilled in the art from a consideration of the following detailed description taken in combination with the accompanying drawings.

BRIEF DESCRIPTION OF THE DRAWINGS

In the drawings, which illustrate what are currently considered to be the best modes for carrying out the invention.

MODES FOR CARRYING OUT THE INVENTION

Reference will now be made to the drawings in which the various elements of the invention will be given numerical designations and in which the invention will be discussed so as to enable one skilled in the art to make and use the invention. It is to be understood that the following description is only exemplary of the principles of the present invention, and should not be viewed as narrowing the claims which follow.

Figures 1, 2:
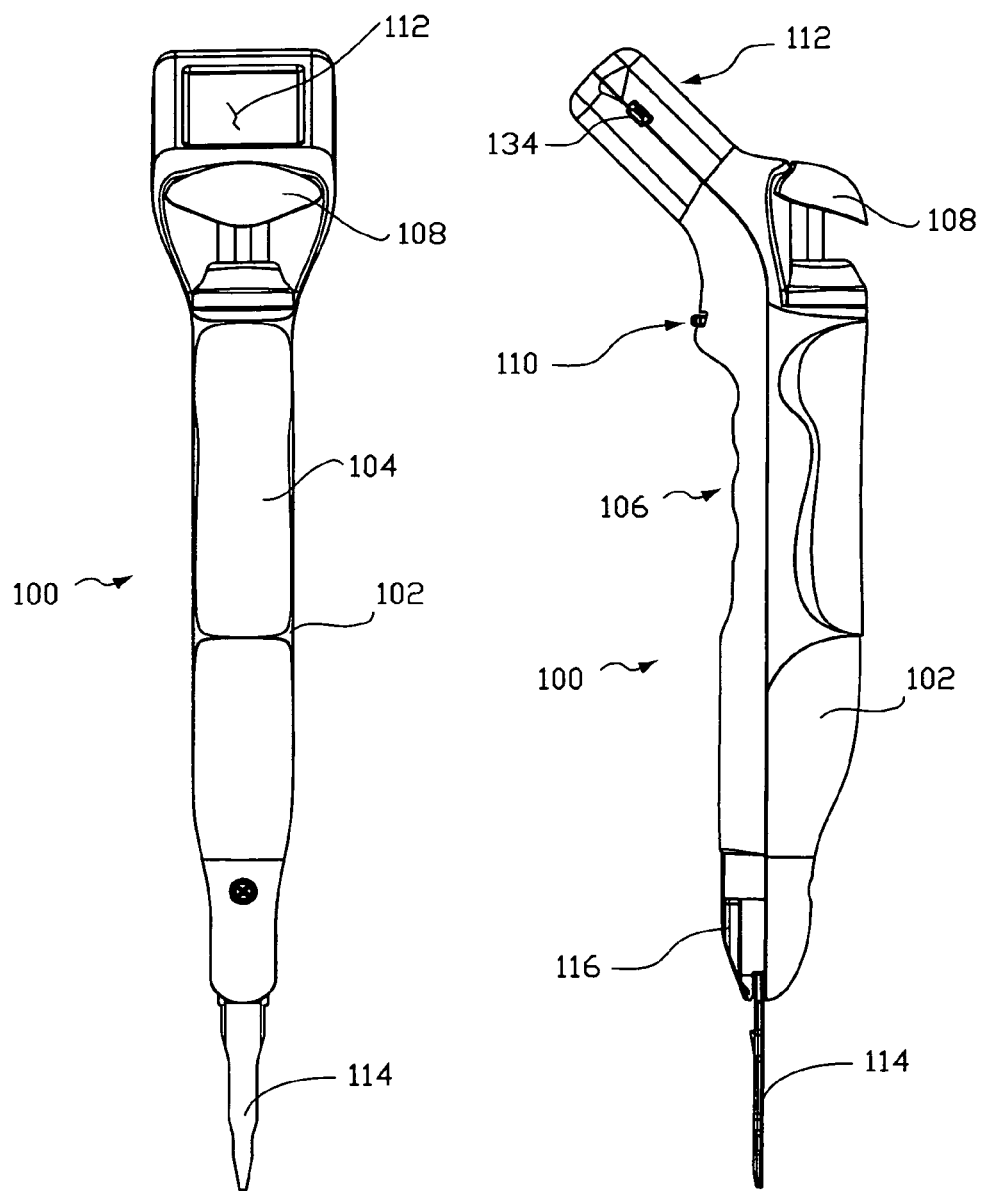
FIG. 1 is a front view in elevation of a pipette instrument structured according to certain principles of the instant invention.
FIG. 2 is a side view in elevation of the pipette illustrated in FIG. 1.

With reference to FIGS. 1 and 2, a pipette structured according to certain principles of the instant invention is indicated generally at 100. Pipette 100 includes a generally cylindrical, extended body 102. A surface of body 102 is structured to form a palm gripping area 104 and a finger gripping area, generally 106.

The illustrated pipette 100 includes a plurality of controls forming a system to receive a user input, including button 108, and scroll wheel 110. As illustrated, button 108 is disposed for user actuation by a user's thumb during one-handed operation of pipette 100. Scroll wheel 110 is disposed to fit under a user's finger, such as the pointer finger, and may be actuated by rolling along a length axis of a finger of a hand that is holding the body 100. A currently preferred scroll wheel 110 is also adapted to receive actuation by depressing the entire wheel with a finger tip, similar to pulling the trigger of a handgun. A display device 112 may be included, e.g. to indicate selection choices to a user, and to show data results.

A distal end of pipette 100 is structured to receive one of a plurality of pipette tips, such as the installed tip 114. Pipette tip 114 may be characterized as an instrumented pipette tip, in that provisions are made for the tip 114 to cooperate with the pipette 100 to interrogate particles as fluid is inspired through the tip 114. In general, instrumented pipette tips that cooperate with a pipette instrument are used once, then discarded. A tip interface module, generally 116, may be provided to facilitate regular maintenance of a pipette instrument, such as pipette 100, as will be described in more detail below.

Figure 3:
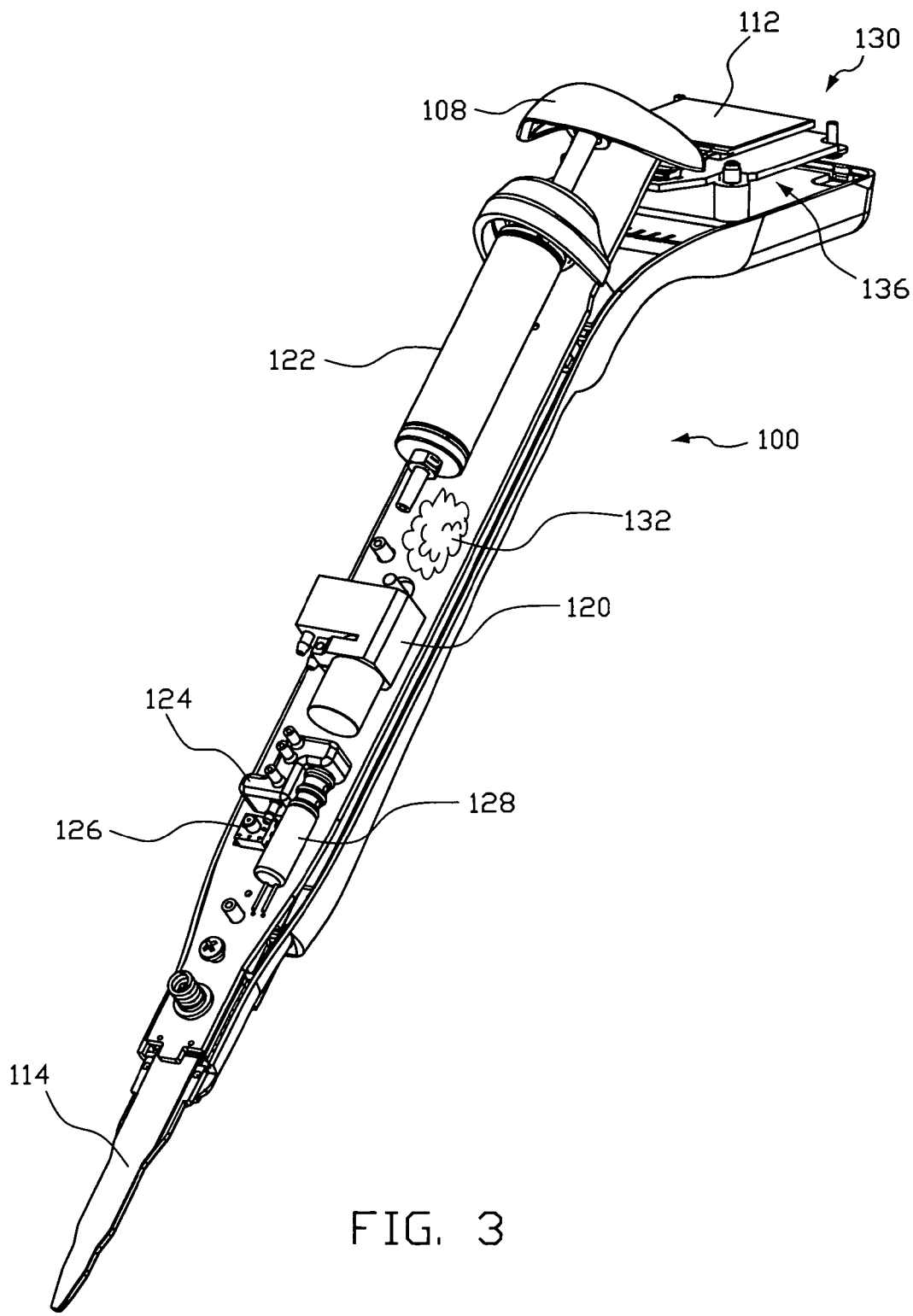
FIG. 3 is a front view in perspective from the right side of the pipette instrument of FIG. 1, partially disassembled.
Figure 4:
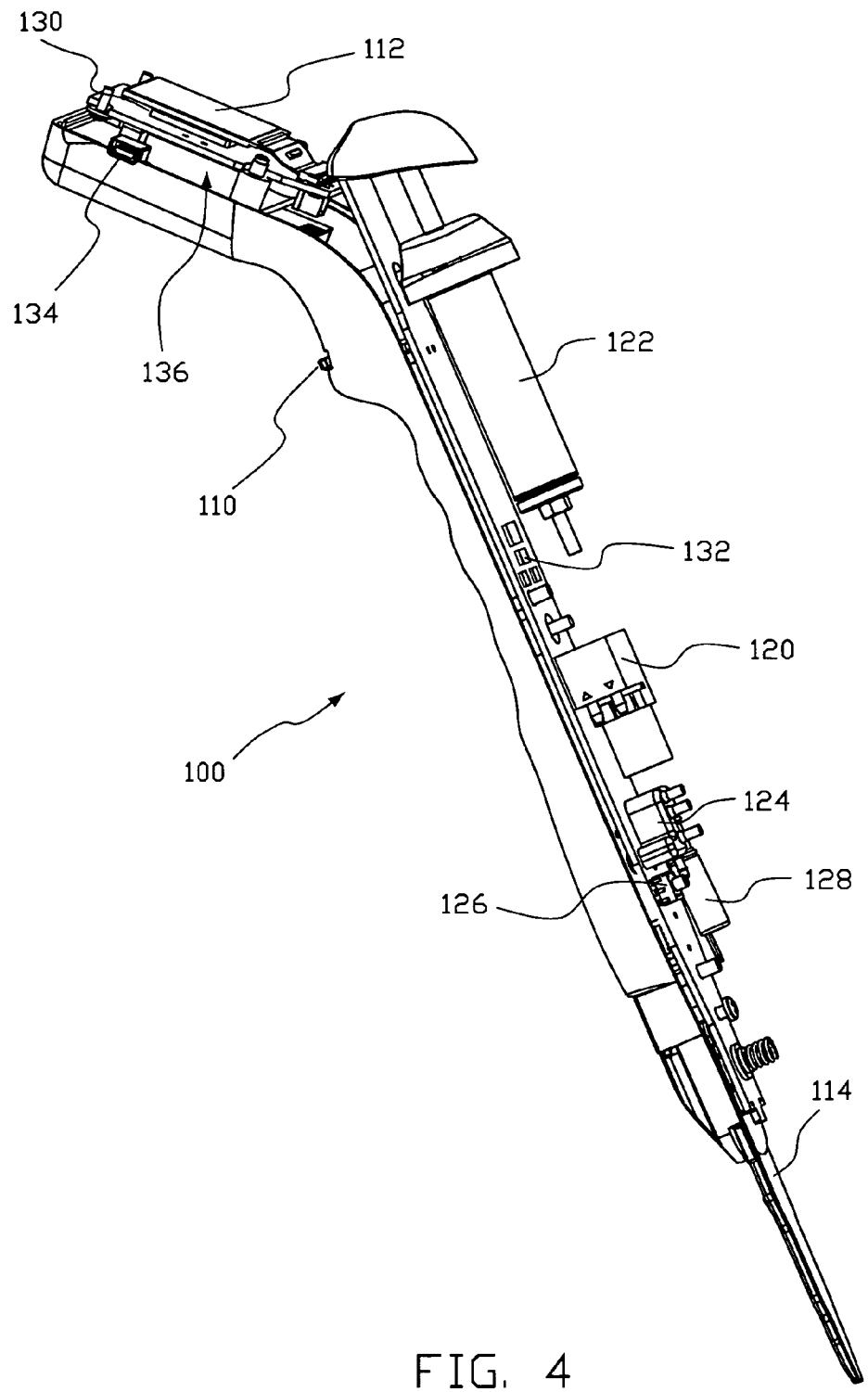
FIG. 4 is a left side view in perspective of the pipette of FIG. 3.

With particular reference now to FIGS. 3 and 4, certain details of construction of an operable pipette instrument 100 will be pointed out. The body of pipette 100 houses a vacuum pump 120 disposed in-circuit with the button 108 to effect a suction on an installed pipette tip. In embodiment 100, button 108 serves as a familiar interface to a user of a conventional hand-held pipette instrument. An air reservoir 122 and pneumatic manifold 124 are used to regulate a pressure profile that is applied over a time increment to a pipette tip, such as tip 114. Pressure transducer 126 provides a feedback signal for the control system. The solenoid valve 128 is used as a purge valve to terminate a suction applied by the pump and reservoir. The control system is orchestrated by a programmable microprocessor and associated memory 130, which can be variously programmed to substantially automatically perform a desired test. Software may be loaded into memory effective to program the microprocessor to permit the pipette instrument to perform a selected test.

The suction system associated with a pipette instrument desirably has an on-board pressure transducer disposed to measure the actual pressure profile that is delivered to a removable pipette tip. To date, three types of suction systems have been built and tested: 1) Generate surplus vacuum using a manually actuated air cylinder and down-regulate using a microprocessor controlled proportional valve and pressure transducer. Vent with a solenoid valve. 2) Generate the vacuum as needed using a microprocessor controlled PID loop with a small vacuum pump (on demand) and a pressure transducer. Vent with a solenoid valve. This is the currently preferred embodiment. It is also desirable to include a "reservoir tank" to dampen the applied vacuum, but that is not critical. 3) Develop surplus vacuum using a pump (store it in a reservoir) and down-regulate using a microprocessor controlled proportional valve and pressure transducer. Vent the vacuum after the profile is applied using a solenoid valve. In this latter case, surplus vacuum may be created by user displacement of a biased element associated with the pipette's body (e.g. mechanically displacing a biased cylinder or diaphragm, etc.).

Interrogation electronics, generally 132, are disposed for connection in-circuit with certain installed pipette tips. Operable interrogation electronics may be configured to detect and/or interpret Coulter principle phenomena, and/or Stokes shift phenomena, which occurs on-board the pipette tip. The interrogation electronics are configured to communicate one or more applied signal to the pipette tip, and relay a resulting signal from the pipette tip to the microprocessor for data manipulation and, typically, display of an output on display device 112. Desirably, a communication link, such as a USB connector 134, wireless transmitter, or other communication device, is provided to facilitate transporting acquired and/or processed test signal data to a remote terminal or storage facility.

Electrical power is desirably provided by a rechargeable electrical power source, such as a battery pack generally indicated at 136. However, it is within contemplation that the device 100 could be embodied as a corded device that receives power from a plug-in electrical utility, such as a wall socket.

Figure 5:
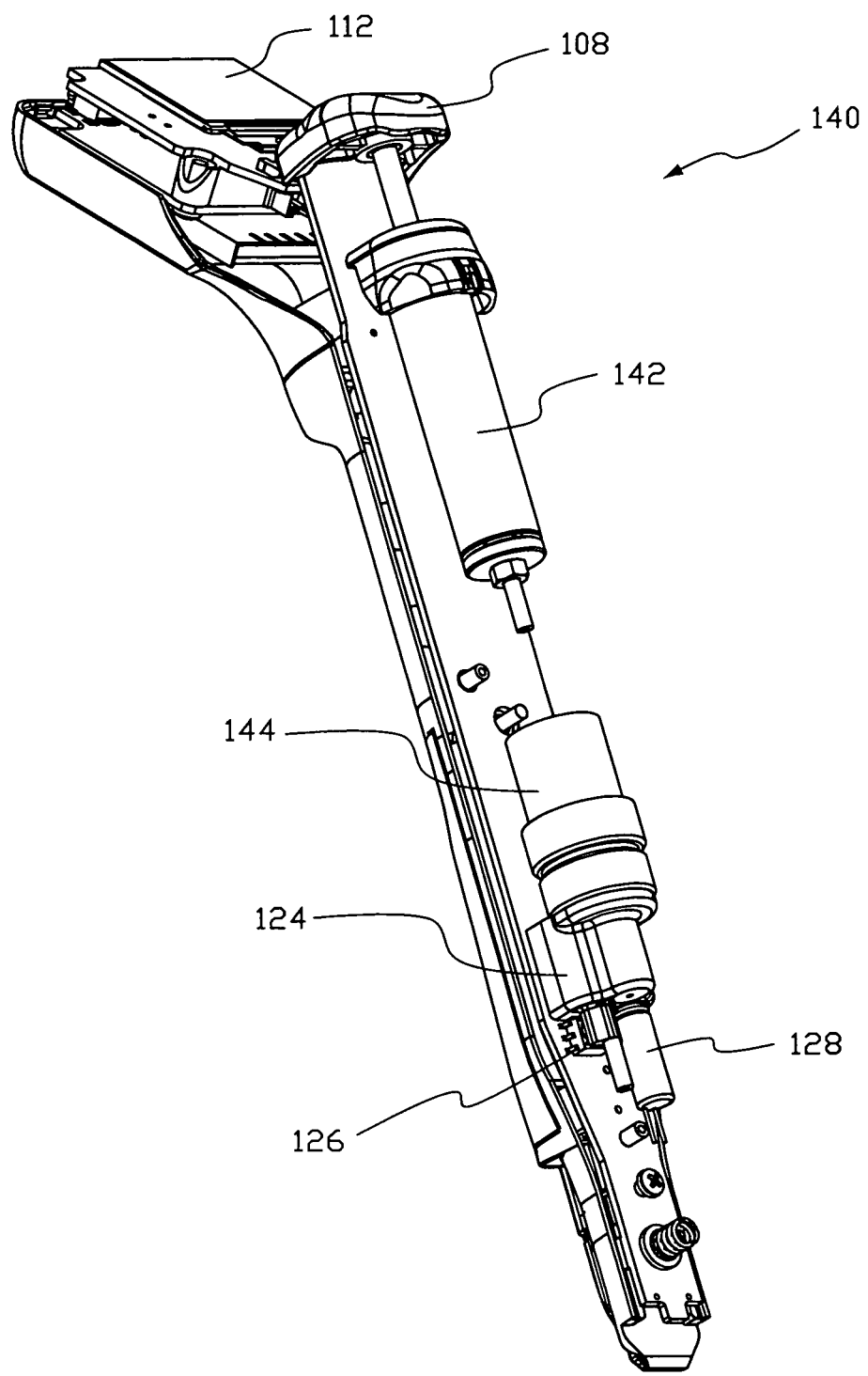
FIG. 5 is a front view in perspective of an alternative pipette instrument, partially disassembled.

FIG. 5 illustrates an alternative arrangement for providing a pressure profile to a pipette tip. The embodiment generally indicated at 140 includes a vacuum cylinder 142 disposed in fluid circuit with a proportional valve 144 and a pneumatic manifold 124. Pressure transducer 126 provides a feedback signal to the microprocessor, which is programmed to apply a desired profile to an installed pipette tip. A purge valve 128 is included in operable fluid circuit to release suction at the completion of an applied pressure profile. Tubing stretches that would place the various components in fluid circuit have been omitted for clarity of illustration.

Figure 6:
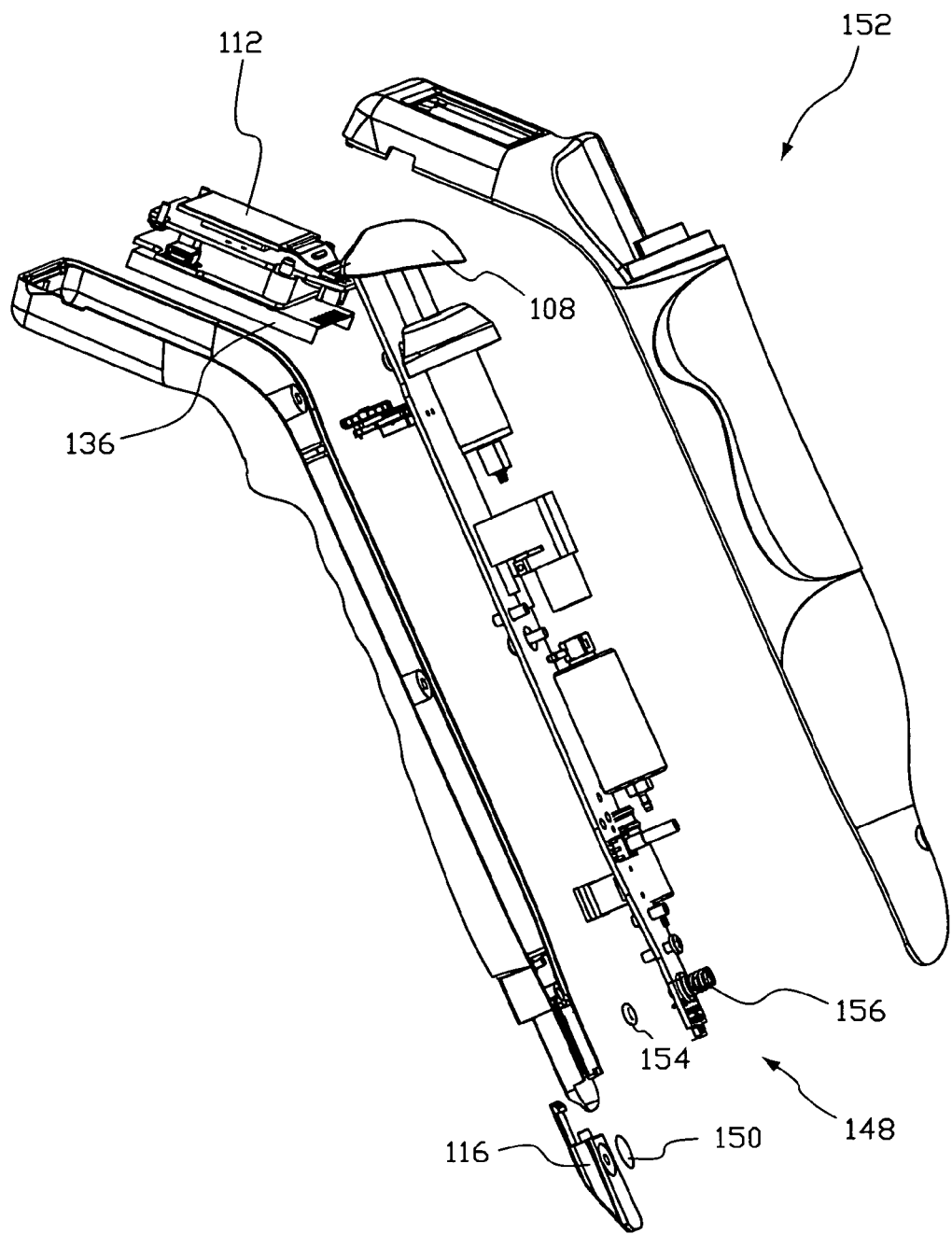
FIG. 6 is an exploded assembly side view in perspective of a pipette instrument structured according to certain principles of the instant invention.

FIG. 6 illustrates certain desirable details of a currently preferred tip interface, generally indicated at 148. A replaceable hydrophobic barrier 150 is carried on removable module 116, and resists fluid flow beyond itself and further into the pipette instrument generally indicated at 152. Therefore, inspired fluid is at least substantially retained inside a removable pipette tip. The O-ring 154 is disposed to form a seal against a face of an installed pipette tip through which to transmit the applied suction profile. A spring 156 may be included to provide a bias to encourage proper and effective seal formation between the O-ring 154 and a cooperating surface of the tip.

Figure 7:
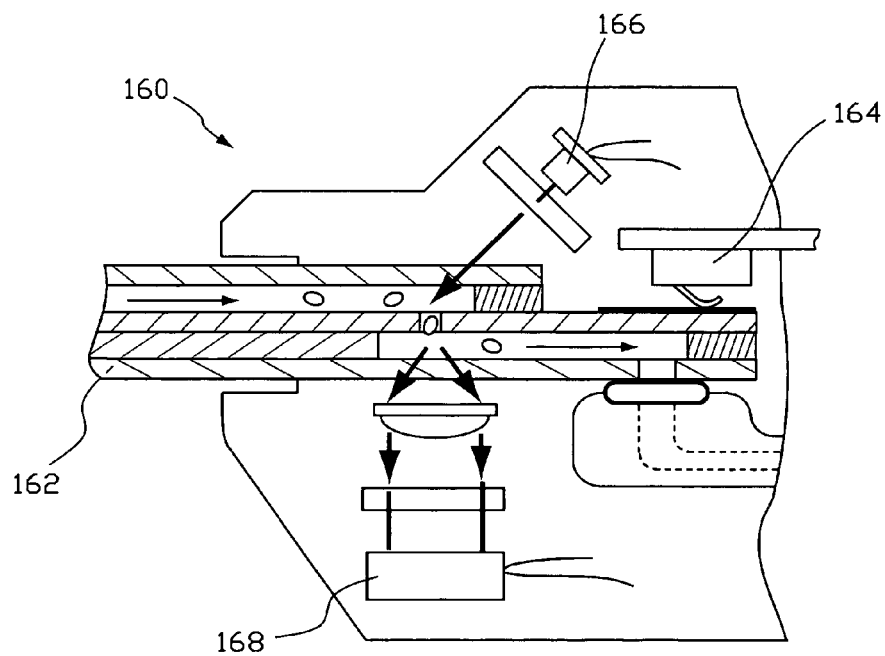
FIG. 7 is a fragmentary side view in section of a portion of a pipette instrument structured according to certain principles of the instant invention.

Certain details of operable pipette tip interfaces are illustrated in FIG. 7. The pipette portion generally indicated at 160 desirably carries orienting structure effective to facilitate coupling with a removable pipette tip 162. An installed tip 162 may be positioned to couple with an optional edge connector 164, effective to place interrogation circuitry into communication with electrodes carried by the tip 162. Therefore, interrogation circuitry may detect and/or interpret Coulter principle phenomena, which occurs on-board the pipette tip as fluid is inspired into the tip 162.

Alternatively, or also, the installed tip 162 may be positioned between a radiation source 166 and a radiation receiver 168. The source 166 and receiver 168 place interrogation circuitry into communication with the pipette tip 162 effective to detect, and/or interpret, Stokes shift phenomena that may occur on-board the pipette tip as fluid is inspired into the tip 162. An operable radiation source may include a fiber optic cable, which permits remote disposition of a radiation source (e.g. laser, LED) at a convenient location of a pipette. Similarly, the receiver may include a fiber optic cable arranged to transport a phase-shifted signal to a radiation detector disposed at a convenient remote location. Locating certain components at a remote location facilitates construction of a more slender pipette tip area.

Figure 8:
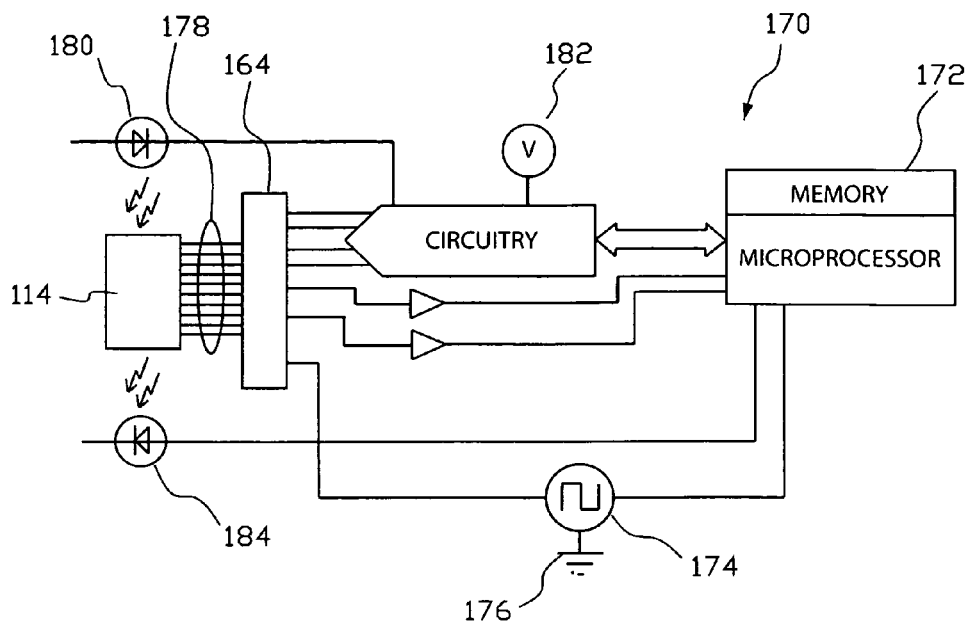
FIG. 8 is a schematic of an operable interrogation circuitry arrangement that may be carried by a pipette instrument structured according to certain principles of the instant invention.

An operable interrogation circuitry is generally indicated at 170 in FIG. 8. A microprocessor and memory 172 desirably are placed into a cooperating operable relationship with the interrogation circuitry 170. One or more electrical signal generator 174 is disposed to apply a signal with reference to ground 176 onto pins, generally 178, of a communication interface for a removable pipette tip 114, such as edge connector 164. A light source 180 may be included to apply a radiation signal to an interrogation zone of a pipette tip. A signal detector, such as ohmmeter 182 and/or light detector 184, is disposed to interrogate corresponding signals received from a tip.

The various pins of connector 164 individually communicate to selected electrodes disposed in the pipette tip. Electrodes carried by a tip 114 may be provided to form stimulated electrodes to apply a signal to fluid flowing through the tip; interrogation electrodes that return a data signal from the tip to the pipette; and trigger electrodes that may be disposed to indicate the location of a fluid wavefront at certain locations disposed along a conduit through the tip. Trigger electrodes can be used, for example, to start and stop a test that is at least partially automated. Electrodes may also be used to provide a continuity signal, for examples: to verify proper installation of a tip in the pipette, or to identify a particular tip and perform a corresponding data collection procedure.

Figure 9:
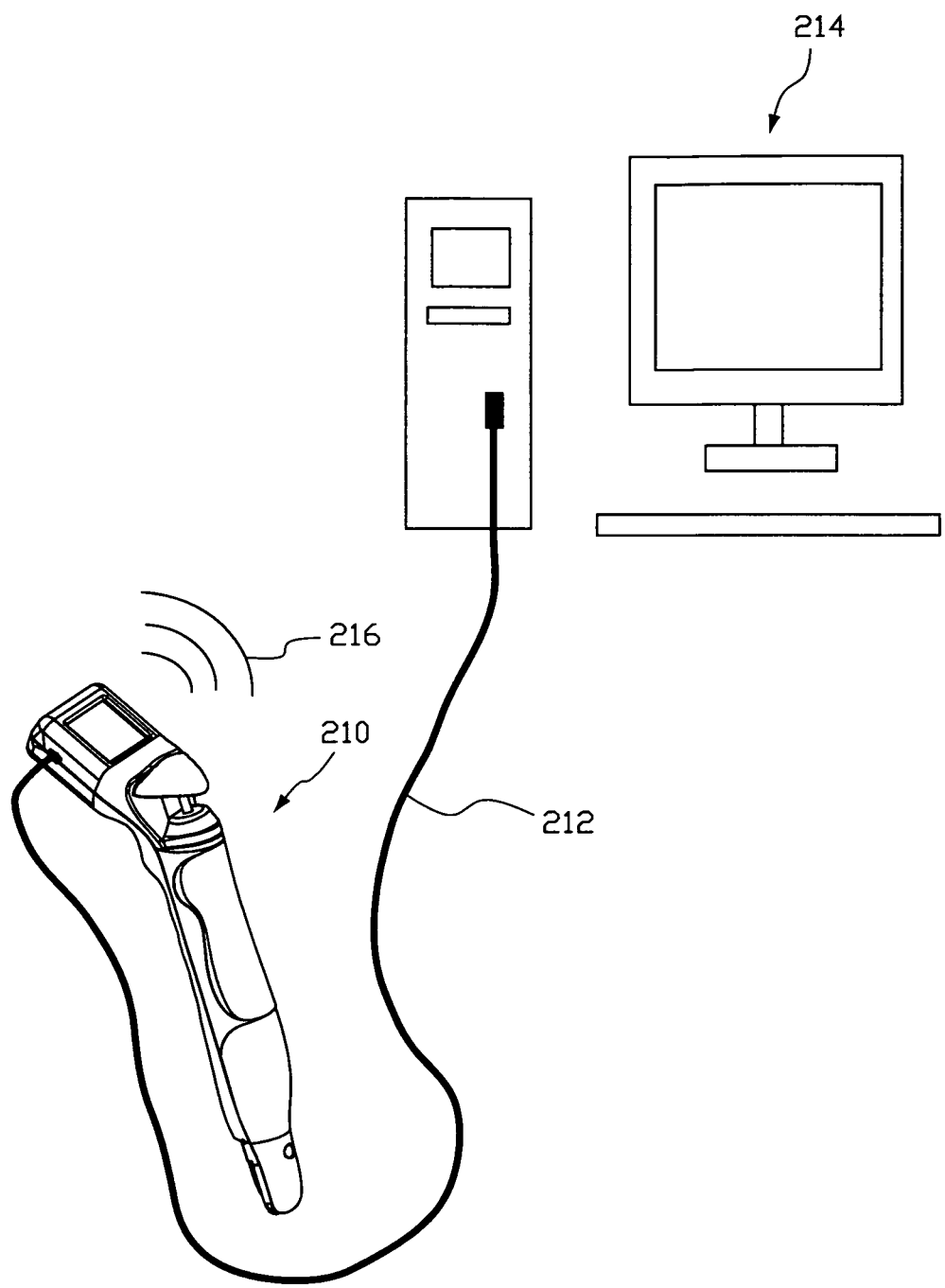
FIG. 9 is a schematic illustrating a workable operating arrangement of a pipette instrument.

FIG. 9 illustrates operation of a representative pipette instrument, generally indicated at 210. The pipette 210 may sometimes be tethered through a cable 212, such as a USB cable, to a remote data receiver 214, such as a personal computer. Test data may be uploaded to the receiver 214 through cable 212, or in certain embodiments, using wireless communication 216.

During a representative particle interrogation test, it is currently preferred to apply a suction pressure profile that starts at about local atmospheric pressure, then ramps to a substantially constant pressure of about 20 inches of $H_2O$ (vacuum) for 2-5 seconds, and then ramps to about 40 inches of $H_2O$ (vacuum) for the remainder of the test. A ramp event is typically effected substantially as a step change in pressure, within the capability of the equipment. However, either a ramp event, or an entire pressure profile, may be structured to apply any function of pressure over any increment of time that is desired in any particular case. Of course, different pressure profiles may be applied to different pipette tips, such as tips that are used for different tests. As a nonlimiting example, tips structured to interrogate larger particles may require a different pressure profile than tips structured to interrogate very small particles. In certain cases, a flat pressure profile, or substantially constant pressure having any operable magnitude, may be applied to obtain workable results for many, if not all, pipette tips.

Figures 10, 11, 12:
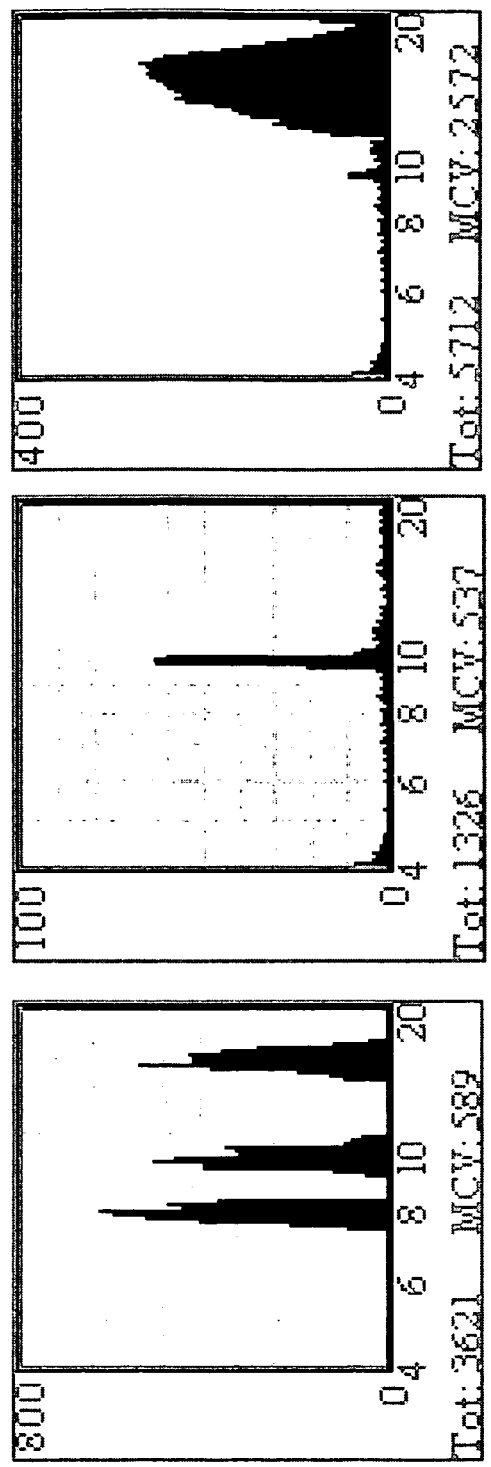
FIGS. 10 through 12 illustrate data obtained in certain operation of a pipette instrument.

FIGS. 10 through 12 are screen shots (histograms) of particle count vs. particle size, and are representative of data that may be obtained and displayed. FIG. 10 is a histograms of a particle suspension containing three differently sized latex beads (8, 10, and 15 μm). FIG. 11 illustrates test results of a suspension of one tight distribution of a single population of precision 10 μm beads. And finally, FIG. 12 is a histograms of a particle suspension containing a population of cultured mamalian cells with an average size of about 16 μm.

To operate a representative pipette: 1) Press/click the track wheel to turn pipette on. 2) Pick up a Tip (insert tip) 3) Depress the main plunger (button 108) 4) Place distal end of tip into liquid sample 5) Release plunger (system automatically starts). 6) User watches as live histogram is formed. 7) Test automatically stops and displays volumetric count for the particles between two user controlled lines on the screen. 8) The track wheel can be scrolled back and forth to move each one of the two lines mentioned above to select the data of interest. 9) Track wheel is click twice fast to exit histogram display screen. 10) Track wheel can be used (scrolling and/or indexing) to navigate through the menus (i.e., saving files, retrieving files, transferring files, etc.). 11) USB cable may be used to recharge the battery and transfer histogram files to a PC.

Figure 13:
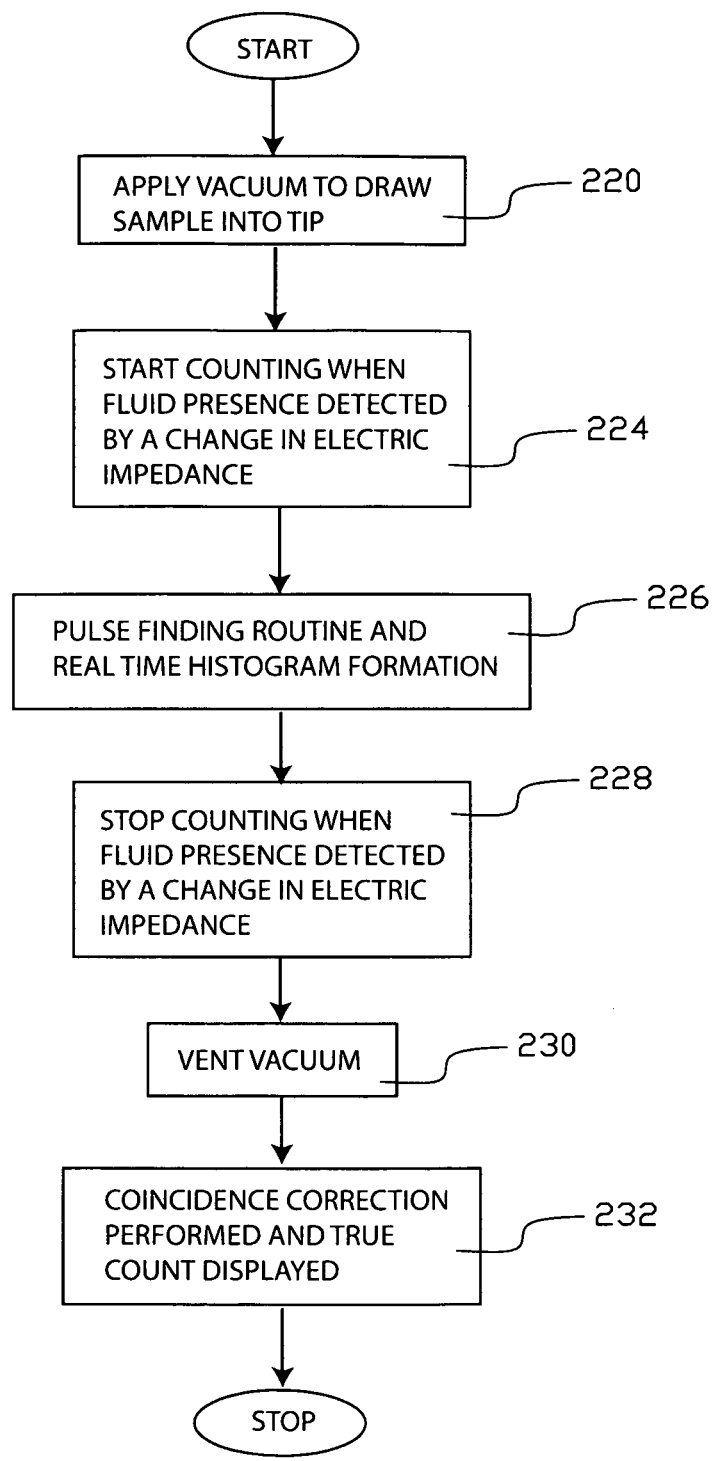
FIG. 13 is a flow chart illustrating certain steps that may be performed in one exemplary operation of a pipette instrument.

Certain desirable operational steps and characteristics are set forth now with reference to FIG. 13. A desired particle test is typically selected by a user by way of a control input, typically with the scroll wheel and with reference to one or more menu presented on display device 112. A pipette tip is installed in a pipette, and the tip is dipped into a bulk container of fluid to be tested. Suction is applied as indicated at step 220. A trigger signal obtained from the pipette tip can be used to start data collection, as indicated at step 224. The microprocessor processes at least one signal obtained from the tip as fluid is inspired, and generates a real-time histogram, as indicated at step 226. A second trigger signal may be used to terminate data collection, as indicated at step 228. Applied suction is then terminated, as indicated at step 230. If desired, coincidence correction may be performed on a displayed piece of data, as indicated at step 232. The pipette tip is typically discarded after a single use.

In a currently preferred embodiment, the data signal (differential voltage in the currently preferred embodiment) is obtained from the tip and is amplified immediately. It is then digitized and run through a real time peak finding (or pulse finding) algorithm by the microprocessor. Currently, peaks over a certain size threshold (i.e., voltage threshold) are detected and the corresponding peak voltage is placed in a "bin" that corresponds to particle size. We currently use 400 separate bins (i.e., individual bars) for the histogram. These bins grow as more and more particles having the same peak voltage are detected. The "observed" particle count is the count obtained right off the raw histogram, usually between two lines (i.e., a lower and upper threshold) that can be positioned by the user. The observed count is coincidence corrected to obtain the "true" count. Observed counts are almost equal to True counts at low particle concentrations. A fudge-factor equation may be used to determine True count from Observed counts. An operable such equation is presented in the paper "Coincidence correction for electrical-zone (Coulter-counter) particle size analysers" by E. J. Wynn and M. J. Hounslow, Department of Chemical Engineering, University of Cambridge, Pembroke Street, Cambridge CB2 3RA, UK.

Pipette tips may be calibrated (for coincidence correction) using serial dilutions of latex beads (as per the above-referenced paper). The user can ALSO calibrate (this is a different type of calibration) the pipette x-axis (particle size) using solutions of latex beads with a known size. This is a manual process where the user dials in the x-axis to match the known bead size.

A representative Coulter-style stimulus signal applied to a pipette tip by the interrogation circuitry includes a signal and a ground. It is currently preferred to supply a source and a sink for a constant-current stimulus using one electrode disposed on each side of an interrogation orifice carried by a pipette tip. The key is to pass a measurable signal through the orifice somehow. While currently preferred to apply a constant current, it is also possible to apply a constant voltage, although not ideal. It is currently preferred to use a DC stimulus, but AC is also possible. At least one measurement electrode is required. It is currently preferred to use two (one disposed on each side of the interrogation orifice), in a differential mode.

While the invention has been described in particular with reference to certain illustrated embodiments, such is not intended to limit the scope of the invention. The present invention may be embodied in other specific forms without departing from its spirit or essential characteristics. The described embodiments are to be considered as illustrative and not restrictive. The scope of the invention is, therefore, indicated by the appended claims rather than by the foregoing description. All changes which come within the meaning and range of equivalency of the claims are to be embraced within their scope.

What is claimed is:

1. A pipette instrument, comprising:
   a body permitting hand-held operation of said instrument to extract a sample from a bulk fluid by inspiring a portion of said bulk fluid into a removable pipette tip that is installed in said instrument, said body carrying:
   a source of suction;
   a pipette tip interface configured to hold a removable pipette tip and place said removable pipette tip into communication with said source of suction;
   a display panel capable of visually presenting information to a user by way of a multi-bar histogram;
   a microprocessor and an associated memory;
   interrogation circuitry in communication with said microprocessor and connectable to an installed pipette tip; and
   a source of electrical energy in operable association with said display panel and said microprocessor; wherein:
   said pipette tip interface is further structured and arranged to dispose an installed pipette tip in communication with said interrogation circuitry to communicate an electrical input signal from said installed pipette tip to said interrogation circuitry such that a value of said electrical input signal may be caused to vary over time responsive to particles entrained in fluid flowing through said installed pipette tip.

2. The pipette instrument according to claim 1, further comprising:
   a hydrophobic barrier element carried on a removable module and adapted to resist flow of fluid from an installed pipette tip past said barrier element and further into said pipette instrument.

3. The pipette instrument according to claim 1, further comprising:
   a user operable control system operable to select a desired mode of operation of said pipette instrument from a plurality of operable modes, said user operable control system comprising a track wheel.

4. The pipette instrument according to claim 3, wherein:
   said track wheel is disposed to interface:
   for actuation by rolling along a length axis of a finger of a hand that is holding said body; and
   in registration with a distal portion of said finger.

5. The pipette instrument according to claim 3, wherein:
   said track wheel is structured to provide an input to said pipette instrument by permitting said finger to depress said track wheel in a trigger-squeezing motion.

6. The pipette instrument according to claim 1, further comprising:

a pressure transducer carried by said body and disposed in communication with said microprocessor to monitor a suction pressure profile delivered to said pipette tip interface.

7. The pipette instrument according to claim 6, wherein:
said source of suction comprises a surplus vacuum in a reservoir; and
a regulator under control of said microprocessor and operable to down-regulate said surplus vacuum is disposed for action between said reservoir and said pipette tip interface effective to place a desired vacuum profile in communication with said installed pipette tip and thereby permit aspiration of a desired fluid sample.

8. The pipette instrument according to claim 6, wherein:
said source of suction comprises an electric pump operable under control of said microprocessor directly to generate an actual desired suction profile delivered to said pipette tip interface, said suction profile including at least two approximately constant values for applied suction that are separated by a ramp event.

9. The pipette instrument according to claim 1, further comprising:
a USB port structured to permit communication between said pipette instrument and a remote terminal.

10. The pipette instrument according to claim 1, further comprising:
a wireless communication module structured to permit communication between said pipette instrument and a remote terminal.

11. The pipette instrument according to claim 1, further comprising:
software that may be loaded into said memory effective to program said microprocessor to permit said pipette instrument to perform a selected test.

12. The pipette instrument according to claim 1, wherein:
said source of electrical energy comprises a battery.

13. A pipette instrument, comprising:
a body carrying:
a source of suction;
a pipette tip interface configured to hold a removable pipette tip and to place an installed pipette tip into communication with said source of suction;
interrogation circuitry adapted for detecting particles moving through a pipette tip that is installed in said pipette tip interface;
a source of electrical energy in operable association with:
a display panel capable of visually presenting information to a user; and
a microprocessor and an associated memory; wherein:
said pipette tip interface is further structured and arranged to dispose an installed said pipette tip in communication with said interrogation circuitry configured to receive an electrical input signal from said installed pipette tip such that a value of said electrical input signal may be caused to vary over time responsive to particles entrained in fluid flowing through said pipette tip; and wherein:
said interrogation circuitry counts particles by detection of signals resulting from Stokes-shift phenomena occurring in said pipette tip.

14. A pipette instrument, comprising:
a body carrying:
a source of suction;
a pipette tip interface configured to hold a removable pipette tip and to place an installed pipette tip into communication with said source of suction;
interrogation circuitry adapted for detecting particles moving through a pipette tip that is installed in said pipette tip interface:
a source of electrical energy in operable association with:
a display panel capable of visually presenting information to a user; and
a microprocessor and an associated memory; wherein:
said pipette tip interface is further structured and arranged to dispose an installed said pipette tip in communication with said interrogation circuitry configured to receive an electrical input signal from said installed pipette tip such that a value of said electrical input signal may be caused to vary over time responsive to particles entrained in fluid flowing through said pipette tip; and wherein:
said interrogation circuitry counts particles by detection of signals resulting from Coulter principle phenomena occurring in said pipette tip.

15. A method for particle counting, comprising:
providing a pipette instrument;
installing a pipette tip in said pipette instrument effective to place a sensor component of said pipette tip in communication with interrogation circuitry associated with said pipette instrument;
applying a first electrical signal to said sensor component;
generating a raw histogram based at least in part upon a second electrical signal received from said sensor component of said pipette tip, said second signal varying over time responsive to flow of a sample of particle-bearing fluid through said pipette tip;
performing a determination based on at least a portion of said raw histogram to obtain one or more observed particle count; and
outputting said one or more observed particle count to a display terminal.

16. The method according to claim 15, further comprising:
selecting a lower threshold boundary;
selecting an upper threshold boundary; and
calculating a particle count based upon data collected between the selected boundaries.

17. The method according to claim 15, further comprising:
performing a mathematical computation on said observed particle count to determine a true particle count.

18. The method according to claim 15, further comprising:
obtaining a corrected histogram based on a mathematical analysis of said raw histogram and a probability that at any instant there is more than one particle in an interrogation zone of said sensor component.

19. The method according to claim 15, further comprising:
applying a correction factor, incorporating one or more calibration histogram associated with said sensor component, to said raw histogram to obtain a particle count.

20. The method according to claim 15, further comprising:
collecting sufficient data to determine a volumetric particle count.

* * * * *